United States Patent [19]
Cast et al.

[11] Patent Number: 5,908,787
[45] Date of Patent: Jun. 1, 1999

[54] TOTAL PROTEIN DETECTION METHOD

[75] Inventors: Todd K. Cast; Michael J. Pugia, both of Granger, Ind.

[73] Assignee: Bayer Corporation, Elkhart, Ind.

[21] Appl. No.: 08/935,977

[22] Filed: Sep. 23, 1997

[51] Int. Cl.$^6$ .................................................. G01N 33/48
[52] U.S. Cl. ............................................. 436/86; 436/169
[58] Field of Search .............................. 436/86, 164, 169, 436/166; 422/56, 61

[56] References Cited

U.S. PATENT DOCUMENTS

| | | |
|---|---|---|
| 4,960,710 | 10/1990 | Lau ......................................... 436/169 |
| 5,055,407 | 10/1991 | Lau et al. ................................ 436/169 |
| 5,087,575 | 2/1992 | Lau ......................................... 436/169 |
| 5,399,498 | 3/1995 | Pugia ....................................... 436/86 |

*Primary Examiner*—Lyle A. Alexander
*Attorney, Agent, or Firm*—Jerome L. Jeffers

[57] ABSTRACT

Disclosed is an improved assay for the determination of total protein in an aqueous test fluid such as urine. The assay involves combining the test fluid with a molybdate or tungstate salt and a dye which forms a complex with molybdate or tungstate ion at a pH of 1.0 to 3.0 to shift the absorption band of the complex in the presence of protein. There is introduced into the assay a substituted phenolsulfonephthalein dye having a pKa which enables it to operate at a pH of from about 1.0 to 3.0 and whose affinity for protein is such that it will provide a detectable response only in the presence of greater than 50 mg/dL of protein to increase the scope of the assay.

9 Claims, No Drawings

TOTAL PROTEIN DETECTION METHOD

BACKGROUND OF THE INVENTION

Methods for the detection of urinary proteins are often more sensitive to albumin than to other urinary proteins. However, it is important to detect proteins other than albumin, especially in the case of Bence-Jones proteinuria. The detection of proteins should cover a wide range of protein concentration since the decision levels and recommended actions to be taken by clinicians will vary depending on the concentration of protein detected in a patient's urine. For example persistent proteinuria greater than 50 mg/dL represents strong evidence of renal disease whereas a protein level of greater than 300 mg/dL is consistent with a diagnosis of nephrotic syndrome. A concentration of protein in urine of greater than 800 mg/dL suggests massive protein loss and warrants a renal biopsy and/or steroid therapy. Accordingly, it is apparent that a test for protein in urine should be effective over a wide range of protein values.

Various methods for the determination of protein in aqueous fluid have been reported in the literature. These methods include the Kjeldahl methods, biuret method, Lowery method, dyestuff combination method, UV method and fluorometric method. In general, proteins react with various substances, particularly with dyes such as bromphenol blue, coomassie brilliant blue and eosine as well as metal ions such as silver (I), copper (II), zinc (II) and lead (II). Typically, the addition of protein to the reaction between a dye and a metal ion results in a spectral change in the dye-metal ion solution. Fujita et al report in Bunseki Kagaku Vol. 32, Pp. E379–E386 that the addition of protein to the reaction between pyrogallol red and molybdenum (VI) produces a different spectrum than that of the pyrogallol red-molybdenum(VI) complex solution. Japanese Kokai Patent No. SHO 62 [1987]-6170 discloses a test strip for protein determination comprising a molybdate salt, a pigment which forms a complex with molybdate and whose absorption band is shifted in the presence of a protein together with a chelating agent which combines with molybdate ions. A similar assay for trace amounts of protein is disclosed in Japanese Kokai Patent 61-155757 in which there is described the use of a chelating agent which is able to bond with molybdenum or a metal ion which is able to bond with oxalic acid, citric acid, phosphoric acid or salts thereof normally present in the urine test sample. This assay is a dye binding method using the complex of pyrogallol red and molybdenum. At low pH the dye-metal complex is red. The color changes to blue when deprotenated at higher pH. The protein causes the dye to deprotenate more easily (at a lower pH) by the interaction of positively charged amino acid groups stabilizing the negatively charged deprotenated dye-molybdate complex.

It has more recently been discovered that tungstate behaves in a manner similar to molybdate in the presence of protein and a dye. Useful molybdate and tungstate salts for the total protein assay of the present invention include sodium, potassium, lithium and ammonium salts or a tungstate/molybdate with an alkyl, dialkyl, trialkyl or tetraalkylammonium ion or a phosphotungstate bearing a similar cation.

In U.S. Pat. No. 5,399,498 there is disclosed the use of certain ionizable phosphate containing compounds to reduce background reactivity in the protein assay which uses a molybdate or tungstate salt and a dye which forms a complex with molybdate or tungstate whose absorption band is shifted in the presence of protein. This reference does not, however, demonstrate that the method can operate over the total range of protein concentrations. U.S. Pat. No. 5,374,561 discloses that nitroso substituted polyhalogenated phenol sulfonephthaleins can be used to detect albumin but does not demonstrate that this dye class can be used in combination with a pyrogallol dye. There is disclosed in U.S. Pat. No. 5,279,790 an analysis method whereby nitro substituted polyhalogenated phenolsulfonephthaleins can be combined with a merocyanine dye to detect albumin.

It would be desirable, and it is an object of the present invention to provide a protein assay based on the interaction of molybdate or tungstate and pyrogallol red which operates over a wide range of protein concentrations.

SUMMARY OF THE INVENTION

The present invention is an improvement to the assay for the determination of total protein in an aqueous test fluid which assay involves combining the test fluid with a molybdate or tungstate salt and pyrogallol red dye which forms a complex with molybdate or tungstate at a low pH, i.e. from about 1.0 to 3.0. In this assay, the absorption band of the complex is shifted in the presence of protein to provide a response which can be detected with a reflectance meter. The present invention involves an improvement to this assay which comprises introducing thereto a substituted sulfonephthalein dye having a pKa which enables it to operate at a pH of from about 1.0 to 3.0 and whose affinity for protein is such that it will provide a detectable response only in the presence of greater than 50 mg/dL of protein in the aqueous test sample.

DESCRIPTION OF THE INVENTION

The assay for protein of the present invention can be carried out in either the wet or dry format. Most conveniently it is carried out in the form of an absorbant test strip impregnated with a buffer, pyrogallol red and a molybdate or tungstate salt as primary indicator and a phenolsulfonephthalein dye as secondary indicator.

Phenolsulfonephthalein indicators particularly useful in the present invention are represented by the following structures, A and B:

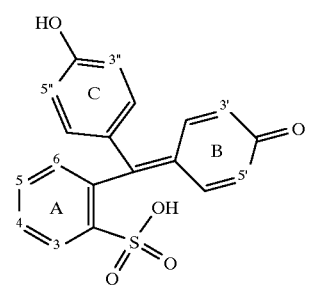

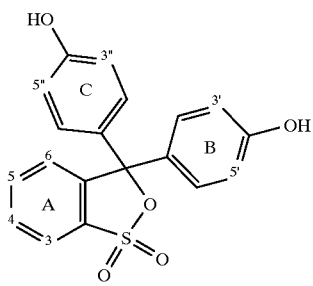

B

Structure A represents the general structure of phenolsulfonephthalein derivatives in protic solvents such as water or an alcohol while structure B represents the form that predominates in the dry state or in aprotic solvents such as ethers and acetonitrile. The phenolsulfonephthalein error indicators are pH indicators which include an ionizable proton having a pKa value such that the proton is displaced by the presence of protein. The pKa value of a phenolsulfonephthalein indicator is the pH at which one half of the number of indicator molecules include the deprotonated C ring phenolic hydroxyl group. In the case of the phenolsulfonephthalein protein error indicators illustrated above, two deprotonation events occur in order to cause an observable color change. The first deprotonation removes the proton from the aryl sulfonic acid on the A ring to yield the ion illustrated below as formula C:

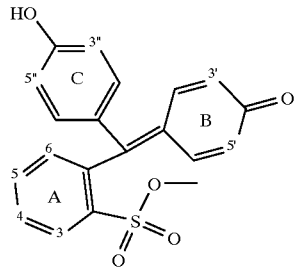

C

The pKa of this proton is less than one, resulting in the ionization of this moiety at all useful pH values. This ionizable group is also responsible for the aqueous solubility of these compounds. The second deprotonation involves the release of a proton from the C ring phenolic hydroxyl to yield the dianion. With this type of protein error indicator, the second deprotonization causes the observable color change which is indicative of the presence of protein in the sample being tested. The phenolsulfonephthalein protein error indicator is typically applied to an absorbent matrix material along with a buffer to provide an environment of constant pH, so that one can rely on the color change being the result of the presence of protein rather than the result of a pH change upon contact with the test fluid. Only those phenosulfonephthalein protein error indicators whose second pKa is such that the second deprotonization takes place at a pH of from about 1.0 to 3.0 are useful in the present invention since it is at this strongly acidic pH that the pyrogallyl red/molybdate or tungstate reaction with protein takes place.

Many phenolsulfonephthalein protein error indicators have their second pKa in the appropriate range and are, therefore, suitable for use in the present invention. Useful phenolsulfonephthaleins include those which are substituted with electron withdrawing and donating groups such as amino, aromatic, alkyl, hydroxyl, carboxylic, alkoxy, acetyl, halogen, nitro or cyanine groups on the A, B or C rings. The particular substituent(s) and their position on the dye molecule are not critical so long as the resulting dye exhibits a pKa in the appropriate range. Unsubstituted phenosulfonephthaleins are not suitable because their pKa's are not in the appropriate range. It has been discovered that the octa substituted sulfonephthalein indicators, i.e. those phenolsulfonephthalein derivatives which are substituted at the 3', 3", 5", 5", 3, 4, 5 and 6 positions, are particularly suitable for use in the present invention. These indicators are preferably substituted with halogen and nitro groups can be represented by the formula:

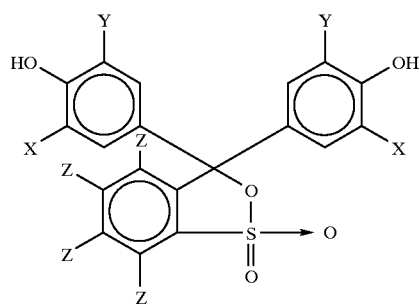

where: X is nitro and Y and Z are chlorine, bromine or iodine. Also useful are the nitro substituted polyhalogenated phenolsulfonephthaleins disclosed in U.S. Pat. No. 5,279,790 wherein Y and Z are nitro. These indicators are said to have the ability to detect from about 2 to 500 mg/dL of protein in a fluid test sample. However, use of the assay system of the present invention would be desirable in situations in which proteinuria greater than 30 mg/dL is to be measured and microalbuminuria at 2 mg/dL is not to be measured. For example, in the case of diagnosing children for renal disease, is it not desirable to measure microalbumin as this response may give a false indication of disease due to its variable nature. It is evident that the aromatic rings of the phenosulfonephthalein indicators useful in the present invention can bear a variety of substituent groups without departing from the scope of the invention. Such substituent groups are limited only by the ability of one of ordinary skill in the art to prepare stable compounds which have the appropriate protein error indicator properties to render them suitable for use in the present invention.

The phenolsulfonephthalein protein error indicators are used in conjunction with the molybdate or tungstate salt assay for protein in which a fluid test sample is combined with a molybdate or tungstate salt and a dye which forms a complex therewith whose absorption band is shifted in the presence of protein. As is disclosed in U.S. Pat. No. 5,399,498; tungstate reacts with the indicator to form a complex whose color shifts in the presence of protein in a manner similar to that of molybdenum. This patent also discloses the use of phytic acid or derivatives thereof to reduce background interference in this sort of assay. While this assay is very good at detecting low levels of protein in a fluid test sample such as urine, its resolution drops off dramatically at higher protein concentrations, particularly at protein concentrations greater than about 150 mg/dL. This method is a total protein assay since the response is not dependent on the type of protein present in the test sample. Thus, human serum albumin (HSA) at 15 mg/dL provides the same response as IgG at 15 mg/dL. Since total protein assays are useful in the detection of certain disease states, and the higher the total protein spillover into urine the more serious the potential problem, a total protein assay which provides a detectable response at high protein concentrations is desirable. However, the molybdate/tungstate assay is not effective for the detection of high levels of protein, i.e. above about 150 mg/dL, because of the strong affinity of the dye for protein. The present invention is predicated on the discovery that the addition of a phenolsulfonephthalein as secondary dye is effective to increase the scope of the assay to enable it to provide visual resolution between higher concentrations of protein than is possible with the molybdate/tungstate assay alone. As is apparent from the data presented in Table 1, other types of protein error indicators do not provide this enhanced resolution. This is believed to be the case because the dyes are not color compatible with the red to purple colors of pyrogallol red. Furthermore, only those phenolsulfonephthaleins whose second pKa is within the pH range at which the molybdate/tungstate assay is operable are suitable for use as the second indicator. An additional requirement of suitable phenolsulfonephthaleins is that their affinity for protein is such that a detectable response results only when the dye is exposed to protein at a concentration of greater than 50 mg/dL. This is the case because dyes with higher affinities will bind to the protein in preference to the pyrogallol red.

The method of practicing the present invention is further illustrated by the following example:

EXAMPLE I

The protein reagents used in this experiment were made from one saturation of J. C. Binzer T467 filter paper with an aqueous/methanol mix containing a buffer (succinic acid), pyrogallol red, sodium molybdate and phytic acid. A second indicator dye, as shown in Table 1, was added. The mix pH was adjusted to 1.5 using sodium hydroxide and/or hydrochloric acid. The mixture may contain any number of surfactants, detergents, background dyes, enhancer polymers or chelating agents which are known in the art for use in conjunction with protein detection methods based on dye binding. After saturation, the filter paper was cut into strips and tested for protein response at various concentrations of protein.

The responses of the pyrogallol red method for human serum albumin (HSA) at 0, 15, 50, 150 and 450 mg/dL in urine were measured in the presence and absence of several types of secondary dyes. This was accomplished by visual measurement using a color scale and comparing colors developed in standard solutions.

The results using each dye combination (and a control in which there was no secondary dye) were visually rated as 0 for no resolution up to 3 for excellent resolution. The results of this experiment are tabulated in Table 1.

TABLE 1

Comparison of Secondary Dyes

| | Secondary Dye | Reagent Response to Protein Expressed as Visual Resolution Between Levels (mg/dL) | | | | Ka | |
|---|---|---|---|---|---|---|---|
| | | 0–15 | 15–50 | 50–150 | 150–450 | pKa | (× $10^5$) |
| 0 | No secondary dye | 2 | 2 | 1 | 0 | — | — |
| 1 | Bromophenol blue | 2 | 2 | 1 | 0 | 3.7 | −5 |
| 2 | Tetrabromophenol blue | 2 | 2 | 1 | 0 | 3.5 | −5 |
| 3 | Bromochlorophenol blue | 2 | 2 | 1 | 0 | 3.8 | −5 |
| 4 | Tetraiodophenolsulfonephthalein | 2 | 2 | 1 | 0 | 4.0 | −5 |
| 5 | 5',5"-Dinitro-3',3"-Diiodo-3,4,5,6-Tetrabromophenolsulfonephthalein | 3 | 2 | 1 | 0 | 1.5 | −65 |
| 6 | 5',5"-Dinitro-3',3",3,4,5,6-hexabromophenolsulfonephthalein | 3 | 3 | 2 | 0 | 1.6 | −5 |
| 7 | 5'-Nitro-5"-Iodo-3',3"3,4,5,6-hexabromophenolsulfonephthalein | 3 | 2 | 3 | 2 | 1.6 | −5 |
| 8 | Merocyanine dye | 2 | 1 | 0 | 0 | 1.5 | 1 |

0 = No resolution  2 = Good resolution
1 = Slight resolution  3 = Excellent resolution The predominant protein found in the urine of diabetics is albumin. Accordingly, the model system for protein urine testing is albumin.

From Table 1, it can be determined that the optimal resolution was obtained with dyes 6 and 7. Secondary dyes 1–4 did not improve resolution between 150 and 450 mg/dL protein because these dyes had too high of a pKa, i.e. outside of the range of 1 to 3. Accordingly, it can be seen that the secondary phenolsulfonephthalein dye must have a lower affinity for protein and only detect concentrations of greater than 50 mg/dL, as in the case of secondary dyes 6 and 7. The secondary phenolsulfonephthalein dye does not prevent the pyrogallol red-molybdate/tungstate dye from binding protein thereby allowing both to interact to give a distinctive result over a broader range of protein concentrations. Secondary dye 5 did not improve resolution between 150 and 450 mg/dL of protein even though it has a pKa of 1.5 because this dye had too high an affinity for proteins in the range of 0–50 mg/dL. On the other hand, secondary dye 8 which has a very low affinity (only detecting protein at > than 150 mg/dL) did not improve resolution. In this case, the pyrogallol red dye which has a higher affinity for protein, binds the protein in preference to secondary dye 8.

The basic components of the assay system of the present invention are pyrogallol red, a molybdate or tungstate salt, a buffer and the phenolsulfonephthalein dye as second indicator. These ingredients are typically dissolved in a protic solvent such as a water/methanol mixture in the concentrations set out in Table 2. Typically, the solution will contain a chelating agent such as phytic acid and/or oxalic acid to prevent interference from other components in the urine test sample.

Applying the solution to an absorbent matrix such as filter paper with drying, results in a test strip which is suitable for detecting protein concentrations in a test fluid over a broader range than could be accomplished with either dye alone.

TABLE 2

Assay Mix Composition

| Ingredient | Function | Conc. Used | Allowable Range |
|---|---|---|---|
| Water | Solvent | 95 mL | — |
| Methanol | Solvent | 5 mL | 0–40 mL |
| Succinic Acid | Buffer | 5.9 g (500 mM) | 50–1000 mM |
| Phytic Acid | Chelator | 1 g (15 mM) | 0–500 mM |
| Pyrogallol Red | Indicator | 28.0 mg (0.7 mM) | 0.03–10 mM |
| Molybdate | Indicator | 24.3 mg (1 mM) | 0.05–10 mM |
| See Table 1 | Second Indicator | 0.3 mM | 0.02–20 mM |
| Oxalic Acid | Chelator | 0.11 g (12 mM) | 0–40 mM |
| pH | — | 1.5 | 1.0–3.0 |

Succinic acid is only one of many buffers which can be used to control the pH. Other suitable buffers include phosphate, oxalic acid, phytic acid, phosphoric acid, citric acid, trichloroacetic acid, benzoic acid, sodium bisulfate, salcylic acid, hydrochloric acid, maleic acid, glycine, phthalic acid, glycylglycine and fumaric acid.

We claim:

1. In an assay for the determination of protein in an aqueous test fluid which comprises combining the test fluid with a molybdate or tungstate salt and pyrogallol red to form a complex with molybdate or tungstate ion and the absorption band of said complex is shifted in the presence of protein to provide a detectable response with good resolution at protein concentrations not greater than about 150 mg/dL, the improvement which comprises introducing into the assay a substituted phenolsulfonephthalein dye having a pKa which enables it to operate at a pH of from about 1.0 to 3.0 and whose affinity for protein is such that it will provide a detectable response only in the presence of greater than 50 mg/dL protein to thereby render the assay suitable for the detection of total protein in the test fluid.

2. The method of claim 1 wherein a buffer, pyrogallol red, a molybdate or tungstate salt, buffer and phenolsulfonephthalein are absorbed in a test strip of absorbant material.

3. The method of claim 1 wherein the phenolsulfonephthalein dye is octasubstituted with amino, aromatic, alkyl, hydroxyl, carboxylic, alkoxy, acetyl, cyanine, halogen, nitro or a combination of these groups.

4. The method of claim 3 wherein the phenolsulfonephthalein dye is substituted at the 5', 5" positions with nitro and at the 3', 3", 3, 4, 5 and 6 positions with chloride, bromide or iodide.

5. A dry device for use in determining protein levels in a fluid test sample which comprises an absorbant material having absorbed therein pyrogallol red, a soluble molybdate or tungstate salt so that when the device is contacted with the fluid test sample there is formed a complex between the pyrogallol red and the molybdate or tungstate the absorbance of which is shifted in the presence of protein to provide a detectable response with the resolution at protein concentrations not greater than about 50 mg/dl protein, a substituted phenolsulfonephthalein dye having a pKa profile which enables it to operate at a pH of from 1.0 to 3.0 and whose affinity for protein is such that it will provide a detectable response only in the presence of greater than 50 mg/dL protein and a buffer system capable of maintaining the pH within the device at a level of from about 1.0 to 3.0 upon contact between the device and the fluid test sample to thereby render the device suitable for the detection of total protein in the fluid test sample.

6. The device of claim 5 wherein the phenolsulfonephthalein dye is octasubstituted with amino, aromatic, alkyl, hydroxyl, carboxylic alkoxy, acetyl, cyanine, halogen, nitro or a combination of these groups.

7. The device of claim 6 wherein the phenolsulfonephthalein dye is substituted at the 5', 5" positions with nitro and at the 3', 3", 3, 4, 5 and 6 positions with chloride, bromide or iodide.

8. The device of claim 5 wherein the sulfonephthalein dye is 5', 5"-Dinitro-3',3",3,4,5,6-hexabromophenolsulfonephthalein or 5'-Nitro-5"-Iodo-3',3",3,4,5,6-hexo bromophenolsulfonephthalein.

9. An assay for the determination of total protein in an aqueous test fluid which comprises combining the test fluid with a molybdate or tungstate salt and pyrogallol red to thereby determine the concentration of protein in the test fluid up to a concentration of about 150 mg/dL and a secondary dye which is 5',5"-Dinitro-3',3",3,4,5,6-Hexabromophenolsulfonephthalein or 5'-Nitro-5"-Iodo-3', 3",3,4,5,6-Hexabromophenolsulfonephthalein to thereby render the assay suitable for the detection of total protein in the test fluid.

* * * * *